(12) United States Patent
Wendel et al.

(10) Patent No.: US 7,204,975 B2
(45) Date of Patent: *Apr. 17, 2007

(54) COSMETIC AND DERMATOLOGICAL LIGHT-PROTECTIVE FORMULATIONS WITH A CONTENT OF PARTICULATE UV-FILTER SUBSTANCES AND ALKYLNAPHTHALATES

(75) Inventors: Volker Wendel, Frankfurt am Main (DE); Anja Göppel, Hamburg (DE); Jens Schulz, Schenefeld (DE)

(73) Assignee: Beiersdorf AG, Hamburg (DE)

( * ) Notice: Subject to any disclaimer, the term of this patent is extended or adjusted under 35 U.S.C. 154(b) by 352 days.

This patent is subject to a terminal disclaimer.

(21) Appl. No.: 10/789,753

(22) Filed: Feb. 27, 2004

(65) Prior Publication Data

US 2004/0258638 A1 Dec. 23, 2004

Related U.S. Application Data

(63) Continuation of application No. PCT/EP02/08577, filed on Aug. 1, 2002.

(30) Foreign Application Priority Data

Aug. 29, 2001 (DE) ................ 101 41 473

(51) Int. Cl.
*A61K 8/00* (2006.01)
*A61K 8/04* (2006.01)
*A61K 31/53* (2006.01)
*A61Q 17/00* (2006.01)
*A61Q 17/04* (2006.01)
*A61Q 19/00* (2006.01)

(52) U.S. Cl. ............... 424/59; 424/60; 424/400; 424/401; 514/241

(58) Field of Classification Search ........... 424/59, 424/60, 400, 401; 514/241
See application file for complete search history.

(56) References Cited

U.S. PATENT DOCUMENTS

| | | | |
|---|---|---|---|
| 5,993,789 A | 11/1999 | Bonda et al. | |
| 6,113,931 A | 9/2000 | Bonda et al. | |
| 6,126,925 A | 10/2000 | Bonda et al. | |
| 6,129,909 A | 10/2000 | Bonda et al. | |
| 6,180,091 B1 | 1/2001 | Bonda et al. | |
| 6,284,916 B1 | 9/2001 | Bonda et al. | |
| 6,355,230 B2* | 3/2002 | Gers-Barlag et al. | 424/59 |
| 6,355,261 B1 | 3/2002 | Bonda et al. | |
| 6,368,578 B1* | 4/2002 | Gers-Barlag et al. | 424/59 |
| 6,403,067 B1 | 6/2002 | Schamper et al. | |
| 6,440,402 B1* | 8/2002 | Gonzalez et al. | 424/59 |
| 6,468,511 B1 | 10/2002 | Chopra et al. | |
| 6,491,901 B2* | 12/2002 | Gers-Barlag et al. | 424/59 |
| 2001/0022966 A1 | 9/2001 | Gers-Barlag et al. | |
| 2001/0026790 A1 | 10/2001 | Gers-Barlag et al. | |
| 2001/0164296 | 11/2002 | Schamper et al. | |
| 2002/0192172 A1 | 12/2002 | Chopra et al. | |
| 2003/0170284 A1 | 9/2003 | Dorschner et al. | |

FOREIGN PATENT DOCUMENTS

| | | |
|---|---|---|
| DE | 660131 A | 10/1951 |
| DE | 199 49 825 A1 | 4/2001 |
| FR | 2 801 206 A | 5/2001 |
| FR | 2 801 207 A | 5/2001 |
| FR | 2 801 208 A | 5/2001 |
| FR | 2 801 209 A | 5/2001 |
| FR | 2 801 210 | 5/2001 |
| FR | 2 801 213 | 5/2001 |
| WO | WO 02 17873 A | 3/2002 |

OTHER PUBLICATIONS

"Eurekalert", 'Online!, Jun. 8, 2001, Gefunden im Internet: url:http://sunsitel.dc.stanford.org/releases/acs-irr3060801.html, 'gefunden am Feb. 12, 2002.

"Beauty is Skin Deep", Happi, 'Online!, Sep. 2000, Gefunden im Internet: url:http://www.happi.com/special/sep002.html, 'gefunden am, Feb. 12, 2002.

International Search Report from corresponding International Application No. PCT/EP02/08577, dated Dec. 20, 2002.

(Continued)

*Primary Examiner*—Shelley A. Dodson
(74) *Attorney, Agent, or Firm*—Greenblum & Bernstein, P.L.C.

(57) ABSTRACT

Cosmetic or dermatological formulations comprising at least one particulate UV filter substance and at least one dialkyl naphthalate having the structural formula

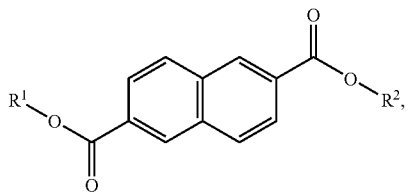

wherein $R^1$ and $R^2$ are selected independently of one another from the group consisting of branched and unbranched alkyl groups having 6 to 24 carbon atoms, are useful for protecting skin from harmful effects of solar radiation, particularly from UV-A and UV-B radiation.

26 Claims, No Drawings

OTHER PUBLICATIONS

German Search Report dated Mar. 27, 2002 for German Appl. DE 101 41 472.2.
German Search Report dated Apr. 12, 2002 for German Appl. DE 101 41 473.0.
Bonda C Et Al: "A New Photostabilizer For Full Spectrum Sunscreens" Cosmetics & Toiletries, Wheaton, IL, US, vol. 115, No. 6, 2000, pp. 37-45.
International Search Report from corresponding International Application No. PCT/EP02/09309 dated Sep. 30, 2003.
International Search Report from corresponding International Application No. PCT/EP02/09374 dated Sep. 30, 2003.
International Search Report from corresponding International Application No. PCT/EP02/09375 dated Dec. 10, 2002.
International Search Report from corresponding International Application No. PCT/EP02/09567, dated Sep. 30, 2003.
International Search Report from corresponding International Application No. PCT/EP02/09543 dated Oct. 2, 2003.
International Search Report from corresponding International Application No. PCT/EP02/009310 dated Apr. 12, 2002.
German Search Report for 101 41 474.9 dated Apr. 15, 2002.
German Search Report for 101 41 478.1 dated Apr. 15, 2002.
German Search Report for 101 41 475.7 dated Jul. 19, 2002.

* cited by examiner

COSMETIC AND DERMATOLOGICAL LIGHT-PROTECTIVE FORMULATIONS WITH A CONTENT OF PARTICULATE UV-FILTER SUBSTANCES AND ALKYLNAPHTHALATES

CROSS-REFERENCE TO RELATED APPLICATIONS

This is a continuation application of PCT/EP02/08577, filed Aug. 1, 2002, which is incorporated herein by reference in its entirety, and also claims the benefit of German Priority Application No. 101 41 473.0, filed Aug. 29, 2001.

FIELD OF THE INVENTION

The present invention relates to cosmetic and dermatological light protection preparations.

BACKGROUND OF THE INVENTION

The harmful effect of the ultraviolet part of solar radiation on the skin is generally known. The rays have various effects on the skin as an organ depending on their particular wavelength; so-called UV-C radiation with a wavelength below 290 nm is absorbed by the ozone layer in the earth's atmosphere and therefore has no physiological significance. By contrast, rays in the range between 290 nm and 320 nm, the so-called UV-B range, cause erythema, simple sunburn or even more or less severe burns. The narrower range around 308 nm is stated to be a maximum for the erythema activity of sunlight.

Numerous compounds are known for protecting against UV-B radiation, examples thereof being derivatives of 3-benzylidenecamphor, of 4-aminobenzoic acid, of cinnamic acid, of salicylic acid, of benzophenone, and of triazine.

It has long been incorrectly assumed that the long-wavelength UV-A radiation with a wavelength between 320 nm and 400 nm has only a negligible biological effect. However, it has now been proved by many studies that UV-A radiation is far more hazardous than UV-B radiation in relation to the initiation of photodynamic, specifically phototoxic, reactions and chronic changes in the skin. It is also possible for the harmful effect of UV-B radiation to be enhanced by UV-A radiation.

Thus, it has been proved, inter alia, that even UV-A radiation under entirely normal everyday conditions is sufficient to damage within a short time the collagen and elastin fibers which are of essential importance for the structure and firmness of the skin. This results in chronic light-induced skin changes—the skin "ages" prematurely. The clinical appearance of skin aged by light includes, for example, creases and wrinkles and an irregular, furrowed relief. In addition, the areas affected by light-induced skin aging may have irregular pigmentation. The formation of brown spots, keratoses and even carcinomas or malignant melanomas is also possible. Skin aged prematurely by everyday exposure to UV is additionally distinguished by a lower activity of the Langerhans cells and a slight chronic inflammation.

About 90% of the ultraviolet radiation which reaches the earth consists of UV-A rays. Whereas UV-B radiation varies greatly depending on a large number of factors (for example season and time of day or latitude), UV-A radiation remains relatively constant from day to day irrespective of seasonal and diurnal or geographic factors. At the same time, most of the UV-A radiation penetrates into living epidermis, while about 70% of UV-B rays are retained by the stratum corneum.

It is therefore of fundamental importance that cosmetic and dermatological light protection preparations provide adequate protection both against UV-B and against UV-A radiation.

In general, the light absorption characteristics of light protection filter substances are very well known and documented, especially since most industrialized countries have positive lists for the use of such substances, which impose very strict standards on the documentation.

Effective UV protection can also be achieved with the aid of organic or inorganic particulate UV filter substances. The protective effect toward UV rays in this case increases as the size of the particles employed decreases. The reduction in particle size simultaneously has the effect that visible light is transmitted, which is why the formulations appear transparent; an unwanted whitening effect through which the affected areas of skin become distinctly white in color now occurs only with very high particle concentrations on initial application of the cream.

In order to achieve effective protection from the sun with the aid of particulate UV filter substances, it is crucial that the primary particles are retained and the dispersion remains stable. However, the reduction in size of the particles greatly increases the surface area of the particles, so that they are prone to agglomeration owing to the increasing forces of attraction.

Agglomeration of the particles leads, however, to a decrease in the pharmaceutical stability and a reduction in the effectiveness of UV protection by the formulation, and to an increase in the scattering power in the visible region, and thus to the whitening effect. Processing of micropigments therefore requires an optimal formulation and an appropriate production process.

SUMMARY OF THE INVENTION

It was therefore an object of the present invention to eliminate the prior art disadvantages and obtain in a simple manner stable preparations which are distinguished by very effective UV protection and in which particulate UV substances are and remain finely dispersed.

It was surprising and could not have been predicted by the skilled worker that the disadvantages of the prior art are remedied by cosmetic or dermatological preparations which are effective for light protection, characterized in that they comprise
(a) at least one particulate soluble UV filter substance and
(b) at least one dialkyl naphthalate having the structural formula

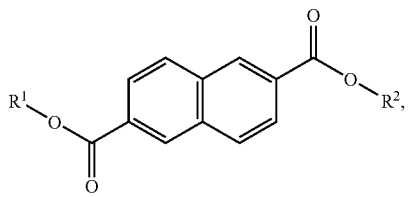

in which $R^1$ and $R^2$ are selected independently of one another from the group of branched and unbranched alkyl groups having 6 to 24 carbon atoms.

The preparations for the purposes of the present invention may, besides one or more oil phases, preferably additionally comprise one or more aqueous phases and be, for example, in the form of W/O, O/W, W/O/W or O/W/O emulsions. Such formulations may preferably also be a microemulsion, a solid emulsions (i.e. an emulsion which is stabilized by solids, e.g. a Pickering emulsion), a sprayable emulsion or a hydrodispersion.

The preparations of the invention are products which are extremely satisfactory in every respect and which are not limited to a restricted choice of raw materials. They are accordingly very particularly suitable for use as basis for preparation forms with diverse application purposes. The preparations of the invention show very good sensory and cosmetic properties such as, for example, the spreadability on the skin or the ability to penetrate into the skin, and are further characterized by very good light protection efficiency with, at the same time, excellent skin care data.

DETAILED DESCRIPTION OF THE PREFERRED EMBODIMENTS

The invention therefore also relates to cosmetic or dermatological preparations which are effective for light protection, characterized in that they comprise synergistic combinations of substances from
(a) at least one particulate UV filter substance and
(b) at least one dialkyl naphthalate having the structural formula

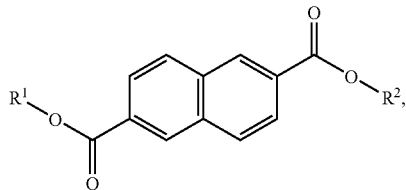

in which $R^1$ and $R^2$ are selected independently of one another from the group of branched and unbranched alkyl groups having 6 to 24 carbon atoms, where the effectiveness of UV protection of these preparations is greater than that of identical preparations which contain no substances specified in (b).

The effectiveness of UV protection by sunscreen compositions or of the UV filters on which they are based is usually determined in biological activity tests under standardized conditions. "Effectiveness of UV protection" means for the purposes of the present invention both the effectiveness of protection from UV-A radiation and from UV-B radiation.

A measure of the effectiveness of UV protection is represented for the purposes of the present invention for example by the sun protection factor (SPF) or else IPD values and the like.

The sun protection factor (SPF) indicates the increased time of exposure to the sun's rays made possible through use of the sunscreen composition. It is the ratio of the erythema threshold time with sunscreen composition to erythema threshold time without sunscreen composition.

The effectiveness of UV-A protection is normally tested by using the IPD method (IPD=immediate pigment darkening). This entails—similar to the determination of the sun protection factor—measurement of a value which indicates how much longer skin protected with the light protection composition can be exposed to UV-A radiation until the same pigmentation occurs as with the unprotected skin.

Another test method which has become established throughout Europe is the Australian standard AS/NZS 2604: 1997. This entails measurement of the absorption of the preparation in the UV-A region. To comply with the standard, the preparation must absorb at least 90% of the UV-A radiation in the range from 320 to 360 nm.

The invention also relates to the use of one or more dialkyl naphthalates having the structural formula

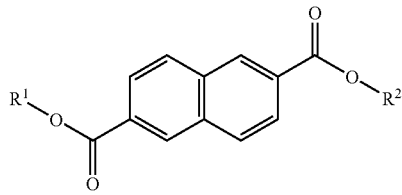

in which $R^1$ and $R^2$ are selected independently of one another from the group of branched and unbranched alkyl groups having 6 to 24 carbon atoms, for increasing the effectiveness of UV protection of cosmetic or dermatological preparations which comprise at least one particulate UV filter substance.

Preferred particulate UV filter substances for the purposes of the present invention are inorganic pigments, especially metal oxides and/or other metal compounds which are slightly soluble or insoluble in water, especially oxides of titanium ($TiO_2$), zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals, and mixtures of such oxides, and the sulfate of barium ($BaSO_4$).

Zinc oxides for the purposes of the present invention may also be used in the form of commercially available oily or aqueous predispersions. Zinc oxide particles and predispersions of zinc oxide particles which are suitable according to the invention are distinguished by a primary particle size of <300 nm and can be obtained under the following proprietary names from the stated companies:

| Proprietary name | Coating | Manufacturer |
|---|---|---|
| Z-Cote HP1 | 2% Dimethicone | BASF |
| Z-Cote | / | BASF |
| ZnO NDM | 5% Dimethicone | H&R |
| ZnO Neutral | / | H&R |
| MZ-300 | / | Tayca Corporation |
| MZ-500 | / | Tayca Corporation |
| MZ-700 | / | Tayca Corporation |
| MZ-303S | 3% Methicone | Tayca Corporation |
| MZ-505S | 5% Methicone | Tayca Corporation |
| MZ-707S | 7% Methicone | Tayca Corporation |
| MZ-303M | 3% Dimethicone | Tayca Corporation |
| MZ-505M | 5% Dimethicone | Tayca Corporation |
| MZ-707M | 7% Dimethicone | Tayca Corporation |

| Proprietary name | Coating | Manufacturer |
| --- | --- | --- |
| Z-Sperse Ultra | ZnO (>=56%)/Ethylhexyl Hydroxystearate Benzoate/Dimethicone/ Cyclomethicone | Collaborative Laboratories |
| Samt-UFZO-450/D5 (60%) | ZnO (60%)/Cyclomethicone/ Dimethicone | Miyoshi Kasei |

Particularly preferred zinc oxides for the purposes of the invention are Z-Cote HP1 and Z-Cote from BASF and zinc oxide NDM from Haarmann & Reimer.

Titanium dioxide pigments of the invention may be in the form of both the rutile and anatase crystal modification and may for the purposes of the present invention advantageously be surface-treated ("coated"), the intention being for example to form or retain a hydrophilic, amphiphilic or hydrophobic character. This surface treatment may consist of providing the pigments by processes known per se with a thin hydrophilic and/or hydrophobic inorganic and/or organic layer. The various surface coatings may for the purposes of the present invention also contain water.

Inorganic surface coatings for the purposes of the present invention may consist of aluminum oxide ($Al_2O_3$), aluminum hydroxide $Al(OH)_3$ or aluminum oxide hydrate (also: alumina, CAS No.: 1333-84-2), sodium hexametaphosphate $(NaPO_3)_6$, sodium metaphosphate $(NaPO_3)_n$, silicon dioxide ($SiO_2$) (also: silica, CAS No.: 7631-86-9), or iron oxide ($Fe_2O_3$). These inorganic surface coatings may occur alone, in combination and/or in combination with organic coating materials.

Organic surface coatings for the purposes of the present invention may consist of vegetable or animal aluminum stearate, vegetable or animal stearic acid, lauric acid, dimethylpolysiloxane (also: dimethicones), methylpolysiloxane (methicones), simethicones (a mixture of dimethylpolysiloxane with an average chain length of from 200 to 350 dimethylsiloxane units and silica gel) or alginic acid. These organic surface coatings may occur alone, in combination and/or in combination with inorganic coating materials.

Coated and uncoated titanium dioxides of the invention may be used in the form of commercially available oily or aqueous predispersions. It may be advantageous to add dispersion aids and/or solubilization mediators.

Suitable titanium dioxide particles and predispersions of titanium dioxide particles for the purposes of the present invention are obtainable under the following proprietary names from the stated companies:

| Proprietary name | Coating | Additional ingredients of the predispersion | Manufacturer |
| --- | --- | --- | --- |
| MT-150W | None | — | Tayca Corporation |
| MT-150A | None | — | Tayca Corporation |
| MT-500B | None | — | Tayca Corporation |
| MT-600B | None | — | Tayca Corporation |
| MT-100TV | Aluminum hydroxide Stearic acid | — | Tayca Corporation |
| MT-100Z | Aluminum hydroxide Stearic acid | — | Tayca Corporation |
| MT-100T | Aluminum hydroxide Stearic acid | — | Tayca Corporation |
| MT-500T | Aluminum hydroxide Stearic acid | — | Tayca Corporation |
| MT-100S | Aluminum hydroxide Lauric acid | — | Tayca Corporation |
| MT-100F | Stearic acid Iron oxide | — | Tayca Corporation |
| MT-100SA | Alumina Silica | — | Tayca Corporation |
| MT-500SA | Alumina Silica | — | Tayca Corporation |
| MT-600SA | Alumina Silica | — | Tayca Corporation |
| MT-100SAS | Alumina Silica Silicone | — | Tayca Corporation |
| MT-500SAS | Alumina Silica Silicone | — | Tayca Corporation |
| MT-500H | Alumina | — | Tayca Corporation |
| MT-100AQ | Silica Aluminum hydroxide Alginic acid | — | Tayca Corporation |
| Eusolex T | Water Simethicone | — | Merck KgaA |
| Eusolex T-2000 | Alumina Simethicone | — | Merck KgaA |
| Eusolex T-Olio F | Silica Dimethylsilate Water | $C_{12-15}$ Alkylbenzoate Calcium Poly-hydroxystearate Silica Dimethylsilate | Merck KgaA |
| Eusolex T-Olio P | Water Simethicone | Octyl Palmitate PEG-7 Hydrogenated Castor Oil Sorbitan Oleate Hydrogenated Castor Oil Beeswax Stearic acid | Merck KgaA |
| Eusolex T-Aqua | Water Alumina Sodium metaphosphate | Phenoxyethanol Sodium Methylparabens Sodium metaphosphate | Merck KgaA |
| Eusolex T-45D | Alumina Simethicone | Isonoyl Isononanuate Polyglyceryl Ricinoleate | Merck KgaA |
| Kronos 1171 (Titanium dioxide 171) | None | — | Kronos |
| Titanium dioxide P25 | None | — | Degussa |
| Titanium dioxide T805 (Uvinul $TiO_2$) | Octyltri-methylsilane | — | Degussa |
| UV-Titan X610 | Alumina Dimethicone | — | Kemira |
| UV-Titan X170 | Alumina Dimethicone | — | Kemira |
| UV-Titan X161 | Alumina Silica Stearic acid | — | Kemira |

-continued

| Proprietary name | Coating | Additional ingredients of the predispersion | Manufacturer |
| --- | --- | --- | --- |
| UV-Titan M210 | Alumina | — | Kemira |
| UV-Titan M212 | Alumina | Glycerol | Kemira |
| UV-Titan M262 | Alumina Silicone | — | Kemira |
| UV-Titan M160 | Alumina Silica Stearic acid | — | Kemira |
| Tioveil AQ 10PG | Alumina Silica | Water Propylene glycol | Solaveil Uniquema |
| Mirasun TiW 60 | Alumina Silica | Water | Rhone-Poulenc |

The titanium dioxides of the invention are distinguished by a primary particle size between 10 nm to 150 nm.

Titanium dioxides particularly preferred for the purposes of the present invention are MT-100 Z and MT-100 TV from Tayca Corporation, Eusolex T-2000 from Merck and titanium dioxide T 805 from Degussa.

Further advantageous pigments are latex particles. Latex particles which are advantageous according to the invention are described in the following publications: U.S. Pat. No. 5,663,213 and EP 0 761 201. Particularly advantageous latex particles are those formed from water and styrene/acrylate copolymers and available for example under the proprietary name "Alliance SunSphere" from Rohm & Haas.

An advantageous organic pigment for the purposes of the present invention is 2,2'-methylenebis(6-(2H-benzotriazol-2-yl)-4-(1,1,3,3-tetramethylbutyl)phenol) (INCI: bis-octyltriazol), which is obtainable under the proprietary name Tinosorb® M from CIBA-Chemikalien GmbH.

It is particularly advantageous for the purposes of the present invention for particulate UV filter substances which are not already in the form of a predispersion first to be dispersed in one or more dialkyl naphthalates of the invention and for this basic dispersion then to be further processed. Whereas auxiliaries which may enter into unwanted interactions with other substances of the cosmetic or dermatological formulation are usually added for stabilization to commercially available predispersions, it is astonishingly possible to dispense with the addition of such stabilizers when preparing basic dispersions of the invention.

The total amount of one or more water-soluble UV filter substances in the finished cosmetic or dermatological preparations is advantageously chosen from the range 0.01% by weight to 20% by weight, preferably from 0.1 to 10% by weight, in each case based on the total weight of the preparations.

Dialkyl naphthalates for which $R^1$ and/or $R^2$ represent branched alkyl groups having 6 to 10 carbon atoms are advantageous for the purposes of the present invention. Very particularly preferred for the purposes of the present invention is diethylhexyl naphthalate, which is obtainable for example under the proprietary name Hallbrite TQ™ from CP Hall or Corapan TQ™ from H&R.

According to the invention, cosmetic or dermatological preparations contain from 0.001 to 20% by weight, advantageously 0.01 to 15% by weight, very particularly preferably 3 to 10% by weight, of one or more dialkyl naphthalates.

The cosmetic or dermatological light-protective formulations of the invention may have conventional compositions and be used for cosmetic or dermatological protection from light, also for the treatment, care and cleansing of the skin and/or hair and as a makeup product in decorative cosmetics.

According to their constitution, cosmetic or topical dermatological compositions can be used for the purposes of the present invention for example as skin protection cream, cleansing milk, day or night cream etc. It is, where appropriate, possible and advantageous to use the compositions of the invention as base for pharmaceutical formulations.

For use, the cosmetic and dermatological preparations are applied in a sufficient quantity to the skin and/or hair in the manner usual for cosmetics.

The cosmetic and dermatological preparations of the invention may contain cosmetic auxiliaries as are customarily used in such preparations, e.g. preservatives, preservative assistants, bactericides, perfumes, substances to prevent foaming, dyes, pigments which have a coloring effect, thickeners, moisturizing and/or humectant substances, fillers which improve the skin feel, fats, oils, waxes or other usual ingredients of a cosmetic or dermatological formulation such as alcohols, polyols, polymers, foam stabilizers, electrolytes, organic solvents or silicone derivatives.

Advantageous preservatives for the purposes of the present invention are, for example, formaldehyde donors (such as, for example, DMDM hydantoin, which is obtainable for example under the proprietary name Glydant™ from Lonza), iodopropylbutylcarbamates (e.g. those obtainable under the proprietary names Glycacil-L, Glycacil-S from Lonza and/or Dekaben LMB from Jan Dekker), parabens (i.e. alkyl p-hydroxybenzoates, such as methyl, ethyl, propyl and/or butyl paraben), phenoxyethanol, ethanol, benzoic acid and more of the like. The preservative system normally also comprises advantageously according to the invention preservative assistants such as, for example octoxyglycerin, glycine soya etc.

Particularly advantageous preparations are also obtained where antioxidants are employed as additives or active ingredients. The preparations advantageously contain according to the invention one or more antioxidants. Favorable antioxidants which may optionally be used are all antioxidants suitable or customary for cosmetic and/or dermatological applications.

It is possible and particularly advantageous for the purposes of the present invention to employ water-soluble antioxidants such as, for example, vitamins, e.g. ascorbic acid and derivatives thereof.

Further preferred antioxidants are vitamin E and derivatives thereof, and vitamin A and derivatives thereof.

The amount of antioxidants (one or more compounds) in the preparations is preferably from 0.001 to 30% by weight, particularly preferably 0.05 to 20% by weight, in particular 0.1 to 10% by weight, based on the total weight of the preparation.

If vitamin E and/or derivatives thereof represent the antioxidant(s), it is advantageous to choose the respective concentrations thereof from the range from 0.001 to 10% by weight based on the total weight of the formulation.

If vitamin A or vitamin A derivatives, or carotenes or derivatives thereof represent the antioxidant(s), it is advantageous to choose the respective concentrations thereof from the range from 0.001 to 10% by weight based on the total weight of the formulation.

It is particularly advantageous for the cosmetic preparations according to the present invention to contain cosmetic or dermatological active ingredients, with preferred active ingredients being antioxidants able to protect the skin from oxidative stress.

Further advantageous active ingredients for the purposes of the present invention are natural active ingredients and/or derivatives thereof, such as, for example, alpha-lipoic acid, phytoene, D-biotin, coenzyme Q10, alpha-glucosylrutin, carnitine, carnosine, natural and/or synthetic isoflavonoids, creatine, taurine and/or β-alanine.

Formulas of the invention containing, for example, known antiwrinkle active ingredients such as flavone glycosides (especially α-glycosylrutin), coenzyme Q10, vitamin E and/or derivatives and the like are particularly advantageously suitable for the prophylaxis and treatment of cosmetic or dermatological skin changes like those occurring for example during skin aging (such as, for example, dryness, roughness and formation of dryness wrinkles, itching, reduced refatting (e.g. after washing), visible dilations of vessels (telangiectasias, cuperosis), flaccidity and formation of creases and wrinkles, local hyperpigmentation, hypopigmentation and abnormal pigmentation (e.g. age spots), increased susceptibility to mechanical stress (e.g. chapping) and the like). They are also advantageously suitable for preventing the appearance of dry or rough skin.

The aqueous phase of the preparations of the invention may advantageously contain conventional cosmetic auxiliaries such as, for example, alcohols, especially those of low C number, preferably ethanol and/or isopropanol, diols or polyols of low C number, and ethers thereof, preferably propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, polymers, foam stabilizers, electrolytes and, in particular, one or more thickeners which can advantageously be chosen from the group of silicon dioxide, aluminum silicates, polysaccharides and derivatives thereof, e.g. hyaluronic acid, xanthan gum, hydroxypropylmethylcellulose, particularly advantageously from the group of polyacrylates, preferably a polyacrylate from the group of so-called carbopols, for example carbopols of types 980, 981, 1382, 2984, 5984, each singly or in combination. It is also possible and preferred to use moisturizers.

Substances or mixtures of substances referred to as moisturizers are those which confer on cosmetic or dermatological preparations the property of reducing the moisture loss from the stratum corneum (also called the transepidermal water loss (TEWL)) and/or have a beneficial effect on the hydration of the stratum corneum, after application or distribution on the surface of the skin.

Advantageous moisturizers for the purposes of the present invention are, for example, glycerol, lactic acid and/or lactates, especially sodium lactate, butylene glycol, propylene glycol, biosaccharides gum-1, glycine soya, ethylhexyloxyglycerin, pyrrolidonecarboxylic acid and urea. It is also particularly advantageous to use polymeric moisturizers from the group of polysaccharides which are soluble in water and/or swellable in water and/or gellable using water. Particularly advantageous are, for example, hyaluronic acid, chitosan and/or a fucose-rich polysaccharide which is listed in chemical abstracts under the registry number 178463-23-5 and is obtainable, for example, under the name Fucogel® 1000 from SOLABIA S.A.

The cosmetic or dermatological preparations of the invention may also advantageously, although not obligatorily, contain fillers which, for example, further improve the sensory and cosmetic properties of the formulations that induce or enhance for example a velvety or silky skin feel. Advantageous fillers for the purposes of the present invention are starch and starch derivatives (such as, for example, tapioca starch, distarch phosphate, aluminum- or sodium-starch octenylsuccinate and the like), pigments which have neither mainly a UV filter effect nor a coloring effect (such as, for example, boron nitride etc.) and/or Aerosils® (CAS No. 7631-86-9).

The oil phase of the formulations of the invention is advantageously chosen from the group of polar oils, for example from the group of lecithins and fatty acid triglycerides, namely the glycerol triesters of saturated and/or unsaturated, branched and/or unbranched alkanecarboxylic acids with a chain length of from 8 to 24, in particular 12 to 18, C atoms. The fatty acid triglycerides can, for example, advantageously be chosen from the group of synthetic, semisynthetic and natural oils such as, for example, coco glyceride, olive oil, sunflower oil, soybean oil, peanut oil, rapeseed oil, almond oil, palm oil, coconut oil, castor oil, wheatgerm oil, grapeseed oil, safflower oil, evening primrose oil, macadamia nut oil and more of the like.

Also advantageous according to the invention are, for example, natural waxes of animal and vegetable origin such as, for example, beeswax and other insect waxes, and berry wax, shea butter and/or lanolin (wool wax).

For the purposes of the present invention, further advantageous polar oil components can also be chosen from the group of esters of saturated and/or unsaturated, branched and/or unbranched alkanecarboxylic acids with a chain length of from 3 to 30 C atoms and saturated and/or unsaturated, branched and/or unbranched alcohols with a chain length of from 3 to 30 C atoms, and from the group of esters of aromatic carboxylic acids and saturated and/or unsaturated, branched and/or unbranched alcohols with a chain length of from 3 to 30 C atoms. Such ester oils can then be advantageously chosen from the group of octyl palmitate, octyl cocoate, octyl isostearate, octyldodeceyl myristate, octyldodecanol, cetearyl isononanoate, isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, stearyl heptanoate, oleyl oleate, oleyl erucate, erucyl oleate, erucyl erucate, tridecyl stearate, tridecyl trimellitate, and synthetic, semisynthetic and natural mixtures of such esters such as, for example, jojoba oil.

The oil phase can advantageously also be chosen from the group of dialkyl ethers and dialkyl carbonates, advantageous examples being dicaprylyl ether (Cetiol OE) and/or dicaprylyl carbonate, for example the one obtainable under the proprietary name Cetiol CC from Cognis.

It is also preferred to choose the oil component(s) from the group of isoeicosane, neopentyl glycol diheptanoate, propylene glycol dicaprylate/dicaprate, caprylic/capric/diglyceryl succinate, butylene glycol dicaprylate/dicaprate, $C_{12-13}$-alkyl lactate, di-$C_{12-13}$-alkyl tartrate, triisostearin, dipentaerythrityl hexacaprylate/hexacaprate, propylene glycol monoisostearate, tricaprylin, dimethylisosorbide. It is particularly advantageous if the oil phase in the formulations of the invention has a content of $C_{12-15}$-alkyl benzoate or consists entirely of the latter.

Further examples of advantageous oil components are butyloctyl salicylate (for example the one obtainable under the proprietary name Hallbrite BHB from CP Hall), hexadecyl benzoate and butyloctyl benzoate and mixtures thereof (Hallstar AB).

Any mixtures of such oil and wax components can also be advantageously employed for the purposes of the present invention.

The oil phase may likewise advantageously also contain nonpolar oils, for example those selected from the group of branched and unbranched hydrocarbons and waxes, in particular mineral oil, Vaseline (petrolatum), liquid paraffin, squalane and squalene, polyolefins, hydrogenated polyisobutenes and isohexadecane. The preferred substances among polyolefins are polydecenes.

The oil phase may also advantageously have a content of cyclic or linear silicone oils or consist completely of such oils, it being preferred, however, to use besides the silicone oil or silicone oils an additional content of other oil phase components.

Silicone oils are high molecular weight synthetic polymeric compounds in which silicon atoms are linked via oxygen atoms in the form of chains and/or networks, and the remaining valences of the silicon are saturated by hydrocarbon radicals (usually methyl groups and less commonly ethyl, propyl, phenyl groups inter alia). The systematic term for silicone oils is polyorganosiloxanes. The methyl-substituted polyorganosiloxanes which represent the most significant compounds in terms of quantity in this group and which have the following structural formula

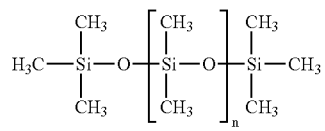

are also referred to as polydimethylsiloxane or dimethicone (INCI). Dimethicones differing in chain lengths and differing in molecular weights exist.

Particularly advantageous polyorganosiloxanes for the purposes of the present invention are, for example, dimethylpolysiloxanes [poly(dimethylsiloxane)], which are obtainable for example under the proprietary names Abil 10 to 10 000 from Th. Goldschmidt. Also advantageous are phenylmethylpolysiloxanes (INCI: phenyl dimethicone, phenyl trimethicone), cyclic silicones (octamethylcyclotetrasiloxane or decamethylcyclopentasiloxane) which are also referred to according to the INCI as cyclomethicones, amino-modified silicones (INCI: amodimethicone) and silicone waxes, e.g. polysiloxane-polyalkylene copolymers (INCI: stearyl dimethicone and cetyl dimethicone) and dialkoxydimethylpolysiloxanes (stearoxy dimethicone and behenoxy stearyl dimethicone) which are obtainable as various types of Abil wax from Th. Goldschmidt. However, other silicone oils can also be used advantageously for the purposes of the present invention, for example cetyldimethicone, hexamethylcyclotrisiloxane, polydimethylsiloxane, poly(methylphenylsiloxane).

It is also advantageous for the purposes of the present invention to produce cosmetic and dermatological preparations whose main purpose is not protection from sunlight but which, nevertheless, comprise a content of further UV-protective substances. Thus, for example, UV-A and UV-B filter substances are usually incorporated into day creams or makeup products. UV-protective substances as well as antioxidants and, if required, preservatives also represent effective protection of the preparations themselves against spoilage. Cosmetic and dermatological preparations which are in the form of a sunscreen composition are also favorable.

Accordingly, the preparations for the purposes of the present invention preferably contain at least one further UV-A, UV-B and/or broad-band filter substance.

The preparations of the invention may also advantageously be in the form of so-called oil-free cosmetic or dermatological emulsions which comprise an aqueous phase and at least one UV filter substance which is liquid at room temperature and/or one or more silicone derivatives as further phase. Oil-free formulations for the purposes of the present invention may advantageously also comprise other lipophilic components—such as, for example, lipophilic active ingredients.

Particularly advantageous UV filter substances which are liquid at room temperature for the purposes of the present invention are homomenthyl salicylate (INCI: homosalate), 2-ethylhexyl 2-cyano-3,3-diphenylacrylate (INCI: octocrylene), 2-ethylhexyl 2-hydroxybenzoate (2-ethylhexyl salicylate, octyl salicylate, INCI: octyl salicylate) and esters of cinnamic acid, preferably 4-methoxycinnamic acid (2-ethylhexyl) ester (2-ethylhexyl 4-methoxycinnamate, INCI: octyl methoxycinnamate) and 4-methoxycinnamic acid isopentyl ester (isopentyl 4-methoxycinnamate, INCI: isoamyl p-methoxycinnamate).

Advantageous further UV filter substances for the purposes of the present invention are sulfonated, water-soluble UV filters such as, for example, phenylene-1,4-bis(2-benzimidazyl)-3,3'-5,5'-tetrasulfonic acid and its salts, especially the corresponding sodium, potassium or triethanolammonium salts, in particular phenylene-1,4-bis(2-benzimidazyl)-3,3'-5,5'-tetrasulfonic acid bissodium salt with the INCI name bisimidazylate (CAS No.: 180898-37-7) which is obtainable for example under the prioprietary name Neo Heliopan AP from Haarmann & Reimer;

salts of 2-phenylbenzimidazole-5-sulfonic acid, such as its sodium, potassium or triethanolammonium salt, and the sulfonic acid itself with the INCI name phenylbenzimidazole sulfonic acid (CAS No. 27503-81-7), which is obtainable for example under the proprietary name Eusolex 232 from Merck or under Neo Heliopan Hydro from Haarmann & Reimer;

1,4-di(2-oxo-10-sulfo-3-bornylidenemethyl)benzene (also: 3,3'-(1,4-phenylenedimethylene)bis(7,7-dimethyl-2-oxo-bicyclo[2.2.1]hept-1-ylmethanesulfonic acid) and its salts (especially the corresponding 10-sulfato compounds, in particular the corresponding sodium, potassium or triethanolammonium salt), which is also referred to as benzene-1,4-di(2-oxo-3-bornylidenemethyl-10-sulfonic acid). Benzene,1,4-di(2-oxo-3-bornylidenemethyl-10-sulfonic acid) has the INCI name terephthalidene dicamphor sulfonic acid (CAS No.: 90457-82-2) and is obtainable for example under the proprietary name Mexoryl SX from Chimex;

sulfonic acid derivatives of 3-benzylidenecamphor such as, for example, 4-(2-oxo-3-bornylidenemethyl)benzenesulfonic acid, 2-methyl-5-(2-oxo-3-bornylidenemethyl) sulfonic acid and salts thereof.

Advantageous UV filter substances for the purposes of the present invention are also so-called broad-band filters, i.e. filter substances which absorb both UV-A and UV-B rays.

Advantageous broad-band filters or UV-B filter substances are, for example, triazine derivatives such as, for example, 2,4-bis-{[4-(2-ethylhexyloxy)-2-hydroxy]phenyl}-6-(4-methoxyphenyl)-1,3,5-triazine (INCI: methylene bis-benzotriazolmethylbutylphenol), which is obtainable under the proprietary name Tinosorb® S from CIBA-Chemikalien GmbH;

dioctylbutylamidotriazone (INCI: diethylhexylbutamidotriazone), which is obtainable under the proprietary name UVASORB HEB from Sigma 3V;
4,4',4''-(1,3,5-triazine-2,4,6-triyltriimino)trisbenzoic acid tris(2-ethylhexyl ester), also: 2,4,6-tris[anilino(p-carbo-2'-ethyl-1'-hexyloxy)]-1,3,5-triazine (INCI: octyl triazone), which is marketed by BASF Aktiengesellschaft under the trademark UVINUL® T 150.

An advantageous broad-band filter for the purposes of the present invention is also 2-(2H-benzotriazol-2-yl)-4-methyl-6-[2-methyl-3-[1,3,3,3-tetramethyl-1-[(trimethylsilyl)oxy] disiloxanyl]propyl]phenyl (CAS No.: 155633-54-8) with the INCI name drometrizole trisiloxane.

The other UV filter substances may be oil-soluble. Advantageous oil-soluble filter substances are, for example:
3-benzylidenecamphor derivatives, preferably 3-(4-methylbenzylidene)camphor, 3-benzylidenecamphor;
4-aminobenzoic acid derivatives, preferably 2-ethylhexyl 4-(dimethylamino)benzoate, amyl 4-(dimethylamino)benzoate;
derivatives of benzophenone, preferably 2-hydroxy-4-methoxybenzophenone, 2-hydroxy-4-methoxy-4'-methylbenzophenone, 2,2'-dihydroxy-4-methoxybenzophenone
and UV filters bound to polymers.

A further light-protective filter substance which can advantageously be used according to the invention is ethylhexyl 2-cyano-3,3-diphenylacrylate (octocrylene) which is obtainable from BASF under the name Uvinul® N 539.

Particularly advantageous preparations for the purposes of the present invention are those which display high or very high UV-A protection, contain, besides the filter substance(s) of the invention, preferably also further UV-A and/or broad-band filters, especially dibenzoylmethane derivatives [for example 4-(tert-butyl)-4'-methoxydibenzoylmethane] and/or 2,4-bis{[4-(2-ethylhexyloxy)-2-hydroxy]phenyl}-6-(4-methoxyphenyl)-1,3,5-triazine, each singly or in any combinations with one another.

The list of UV filters mentioned which can be employed for the purposes of the present invention is, of course, not intended to be limiting.

The preparations of the invention advantageously contain the substances which absorb UV rays in the UV-A and/or UV-B ranges in a total amount of, for example, 0.1% by weight to 30% by weight, preferably 0.5 to 20% by weight, in particular 1.0 to 15.0% by weight, in each case based on the total weight of the preparations, in order to provide cosmetic preparations which protect the hair and skin from the entire range of ultraviolet radiation.

It may also be advantageous where appropriate to incorporate film formers into the cosmetic or dermatological preparations of the invention, for example in order to improve the water resistance of the preparations or to increase the effectiveness of UV protection (UV-A and/or UV-B boosting). Both water-soluble or dispersible and fat-soluble film formers are suitable, each singly or in combination with one another.

Advantageous water-soluble or dispersible film formers are, for example, polyurethanes (e.g. the Avalure® types from Goodrich), dimethicone copolyol polyacrylates (Silsoft Surface® from Witco Organo Silicones Group), PVP/VA (VA=vinyl acetate) copolymer (Luviscol VA 64 powder from BASF) etc.

Advantageous fat-soluble film formers are, for example, the film formers from the group of polymers based on polyvinylpyrrolidone (PVP)

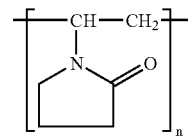

Copolymers of polyvinylpyrrolidone are particularly preferred, for example the PVP hexadecene copolymer and the PVP eicosene copolymer, which are obtainable under the proprietary names Antaron V216 and Antaron V220 from GAF Chemicals Cooperation, and Tricontayl PVP and more of the like.

The following examples are intended to illustrate the present invention without restricting it. The numerical values in the examples mean percentages by weight based on the total weight of the respective preparations.

EXAMPLES

1. O/W Sunscreen Emulsions

|  | 1 | 2 | 3 | 4 | 5 | 6 | 7 |
|---|---|---|---|---|---|---|---|
| Glyceryl monostearate SE | 0.50 | 1.00 | 3.00 |  |  | 1.50 |  |
| Glyceryl stearate citrate | 2.00 |  |  | 1.00 | 2.00 |  | 2.50 |
| Stearic acid |  | 3.00 |  | 2.00 |  |  |  |
| PEG-40 stearate | 0.50 |  |  |  |  | 2.00 |  |
| Cetyl phosphate |  |  |  |  | 1.00 |  |  |
| Stearyl alcohol |  |  | 3.00 |  |  | 2.00 | 0.50 |
| Cetyl alcohol | 2.50 | 1.00 |  | 1.50 | 0.50 |  | 2.00 |
| Ethylhexyl methoxycinnamate |  |  |  | 5.00 | 6.00 |  | 8.00 |
| Bis-ethylhexyloxyphenol methoxyphenyl triazine |  | 1.50 |  | 2.00 | 2.50 |  | 2.50 |
| Butyl methoxydibenzoylmethane | 1.00 | 3.00 | 2.00 | 1.50 | 2.80 | 2.00 | 1.50 |
| Disodium phenyl dibenzimidazole tetrasulfonate | 2.50 | 0.50 | 0.50 | 2.00 | 1.00 | 1.70 | 0.30 |
| Ethylhexyl triazone | 4.00 |  | 3.00 | 4.00 | 4.00 | 2.00 |  |
| 4-Methylbenzylidene camphor | 4.00 | 4.00 |  |  | 2.00 | 4.00 | 2.00 |
| Octocrylene |  |  | 4.00 |  |  |  | 2.50 |
| Diethylhexyl butamido triazone | 1.00 |  |  | 2.00 | 1.00 |  |  |

-continued

| | 1 | 2 | 3 | 4 | 5 | 6 | 7 |
|---|---|---|---|---|---|---|---|
| Phenylbenzmidazole sulfonic acid | 0.50 | | | 3.00 | | | |
| Methylene bis-benzotriazolyl tetramethylbutylphenol | 2.00 | | 0.50 | 1.50 | 2.50 | | |
| Benzophenone-3 | | | | 5.50 | | | |
| Isoamyl p-methoxycinnamate | | 1.50 | | | | | |
| Homosalate | | 2.00 | | | | | |
| Ethylhexyl salicylate | | | 3.00 | | | | 5.00 |
| Drometrizole trisiloxane | | | 0.50 | | | 1.00 | |
| Terephthalidene dicamphor sulfonic acid | | 1.50 | | | 1.00 | 0.50 | |
| Diethylhexyl 2,6-naphthalate | 3.50 | 4.80 | 7.00 | 9.50 | 6.70 | 5.50 | 8.00 |
| Titanium dioxide MT-100Z | | 1.50 | | 3.00 | | 2.00 | |
| Titanium dioxide MT-100TV | 5.0 | | 10.0 | | 2.00 | | |
| Titanium dioxide Eusolex T-2000 | 2.0 | | 2.0 | 7.0 | | | 10.0 |
| Titanium dioxide T805 | | 3.0 | | | 2.00 | 2.00 | |
| Titanium dioxide Eusolex T-Aqua | | | 2.0 | | | | 5.5 |
| Zinc oxide HP1 | | | 1.50 | | | | 4.0 |
| Zinc oxide NDM | 1.0 | | | | | 8.0 | |
| Zinc oxide Neutral | | 5.0 | | 8.0 | 10.0 | | 4.0 |
| Zinc oxide MZ-3035 | 5.0 | | 2.5 | | | | |
| C12–15 alkyl benzoate | | 2.50 | | | 4.00 | 7.00 | 5.00 |
| Dicaprylyl ether | | | 3.50 | | 2.00 | | |
| Butylene glycol dicaprylate/dicaprate | 5.00 | | | 6.00 | | | |
| Dicaprylyl carbonate | | | 6.00 | | | 2.00 | 2.00 |
| Dimethicone | | 0.50 | 1.00 | | 2.00 | | |
| Cyclomethicone | 2.00 | | | 0.50 | | | 0.50 |
| Shea butter | | 2.00 | | | | | 0.50 |
| PVP hexadecene copolymer | 0.50 | | | 0.50 | 1.00 | | 1.00 |
| Tricontanyl PVP | | 0.50 | 1.00 | | | | 1.00 |
| Glycerol | 3.00 | 7.50 | | 7.50 | 5.00 | | 2.50 |
| Xanthan gum | 0.15 | | 0.05 | | | | 0.30 |
| Sodium carbomer | | 0.20 | 0.10 | 0.20 | | | |
| Vitamin E acetate | 0.50 | | 0.25 | | 0.75 | | 1.00 |
| Polyurethane | | 0.50 | | 0.50 | | 1.00 | |
| Styrene/acrylate copolymer | 0.80 | | 3.00 | 1.50 | | | |
| DMDM hydantoin | | 0.60 | 0.40 | 0.20 | | | |
| Konkaben LMB ® | | | | 0.18 | 0.20 | 0.10 | 0.15 |
| Methylparaben | 0.15 | | 0.25 | | 0.50 | | |
| Phenoxyethanol | 1.00 | 0.40 | | 0.40 | 0.50 | 0.40 | 0.60 |
| Ethanol | | 2.00 | 1.50 | | 3.00 | | 1.00 |
| Perfume | 0.20 | 0.20 | 0.20 | 0.20 | 0.20 | 0.20 | 0.20 |
| Water | ad 100 | ad 100 | ad 100 | ad 100 | ad 100 | ad 100 | ad 100 |

2. Hydrodispersions

| | 1 | 2 | 3 | 4 | 5 |
|---|---|---|---|---|---|
| Ceteareth-20 | 1.00 | | | 0.5 | |
| Cetyl alcohol | | | 1.00 | | |
| Sodium carbomer | | 0.20 | | 0.30 | |
| Acrylates/C10–30 alkyl acrylate crosspolymer | 0.50 | | 0.40 | 0.10 | 0.10 |
| Xanthan gum | | 0.30 | 0.15 | | 0.50 |
| Ethylhexyl methoxycinnamate | | | | 5.00 | 8.00 |
| Bis-Ethylhexyloxyphenol methoxyphenyl triazine | | 1.50 | | 2.00 | 2.50 |
| Butyl methoxydibenzoylmethane | 1.00 | 0.50 | 2.00 | 3.00 | 2.50 |
| Disodium phenyl dibenzimidazole tetrasulfonate | 0.50 | 1.80 | 1.50 | 2.00 | 3.00 |
| Ethylhexyl triazone | 4.00 | | 3.00 | 4.00 | |
| 4-Methylbenzylidene camphor | 4.00 | | | 2.00 | |
| Octocrylene | | 4.00 | 3.90 | | 2.50 |
| Diethylhexyl butamido triazone | 1.00 | | | 2.00 | |
| Phenylbenzmidazole sulfonic acid | 0.50 | | | 3.00 | |
| Methylene bis-benzotriazolyl tetramethylbuthylphenol | 2.50 | 0.50 | | | 0.80 |
| Drometrizole trisiloxane | | | 1.00 | | 1.50 |
| Terephthalidene dicamphor sulfonic acid | | 0.50 | | | 1.00 |
| Diethylhexyl 2,6-naphthalate | 4.50 | 8.00 | 7.20 | 5.50 | 9.80 |
| Titanium dioxide MT-100Z | 0.50 | | 2.00 | | 1.00 |
| Titanium dioxide MT-100TV | | 5.0 | | | |
| Titanium dioxide Eusolex T-2000 | | | | 10.0 | |
| Titanium dioxide T805 | 5.5 | | | | 7.5 |
| Titanium dioxide Eusolex T-Aqua | | | 4.5 | | |
| Zinc oxide HP1 | 2.0 | | | 5.5 | |
| Zinc oxide NDM | | 3.0 | | | 5.5 |

-continued

|  | 1 | 2 | 3 | 4 | 5 |
|---|---|---|---|---|---|
| Zinc oxide Neutral | 1.0 |  |  |  | 0.5 |
| Zinc oxide MZ-303S |  | 2.5 |  | 4.5 |  |
| C12–15 alkyl benzoate | 2.00 | 2.50 |  |  |  |
| Dicaprylyl ether |  | 4.00 |  |  |  |
| Butylene glycol dicaprylate/dicaprate | 4.00 |  | 2.00 | 6.00 |  |
| Dicaprylyl carbonate |  | 2.00 | 6.00 |  |  |
| Dimethicone |  | 0.50 | 1.00 |  |  |
| Phenyltrimethicone | 2.00 |  |  | 0.50 | 2.00 |
| Shea butter |  | 2.00 |  |  |  |
| PVP hexadecane copolymer | 0.50 |  |  | 0.50 | 1.00 |
| Tricontanyl PVP | 0.50 |  | 1.00 |  |  |
| Ethylhexylglycerol |  | 1.00 |  | 0.50 |  |
| Glycerol | 3.00 | 7.50 |  | 7.50 | 2.50 |
| Glycine soya |  |  | 1.50 |  |  |
| Vitamin E acetate | 0.50 |  | 0.25 |  | 1.00 |
| Polyurethane |  | 0.60 | 1.50 | 1.00 |  |

-continued

|  | 1 | 2 | 3 | 4 | 5 |
|---|---|---|---|---|---|
| Styrene/acrylate copolymer |  | 2.50 | 0.50 |  | 2.00 |
| DMDM hydantoin |  | 0.60 | 0.40 | 0.20 |  |
| Konkaben LMB ® | 0.20 |  |  |  | 0.15 |
| Methylparaben | 0.50 |  | 0.25 | 0.15 |  |
| Phenoxyethanol | 0.50 | 0.40 |  | 1.00 | 0.60 |
| Ethanol | 3.00 | 2.00 | 1.50 |  | 1.00 |
| Perfume | 0.20 | 0.20 | 0.20 | 0.20 | 0.20 |
| Water | ad 100 | ad 100 | ad 100 | ad 100 | ad 100 |

3. W/O Sunscreen Emulsions

|  | 1 | 2 | 3 | 4 | 5 |
|---|---|---|---|---|---|
| Cetyldimethicone copolyol |  | 2.50 |  | 4.00 |  |
| Polyglyceryl 2-dipolyhydroxystearate | 5.00 |  |  |  | 4.50 |
| PEG 30 dipolyhydroxystearate |  |  | 5.00 |  |  |
| Ethylhexyl methoxycinnamate |  | 8.00 |  | 5.00 | 4.00 |
| Bis-Ethylhexyloxyphenol methoxyphenyl triazone | 2.00 | 2.50 |  | 2.00 | 2.50 |
| Butyl methoxydibenzoylmethane | 0.50 | 3.00 | 2.00 | 1.00 | 0.70 |
| Disodium phenyl dibenzimidazole tetrasulfonate | 0.50 | 1.00 | 1.60 | 2.00 | 2.60 |
| Ethylhexyl triazone |  |  | 3.00 | 4.00 |  |
| 4-Methylbenzylidene camphor |  | 2.00 |  | 4.00 | 2.00 |
| Octocrylene | 0.90 | 2.50 | 3.90 |  | 2.50 |
| Diethylhexyl butamido triazone | 1.00 |  |  | 2.00 |  |
| Phenylbenzmidazole sulfonic acid | 0.50 |  |  | 3.00 | 2.00 |
| Methylene bis-benzotriazolyl tetramethylbutylphenol |  |  | 2.00 | 0.50 |  |
| Drometrizole trisiloxane |  | 1.00 |  |  | 1.50 |
| Terephthalidene dicamphor sulfonic acid |  |  | 1.00 |  | 0.50 |
| Diethylhexyl 2,6-naphthalate | 7.50 | 5.50 | 3.50 | 8.80 | 9.70 |
| Titanium dioxide MT-100Z | 3.0 |  |  |  | 1.5 |
| Titanium dioxide MT-100TV |  | 5.5 |  |  | 2.5 |
| Titanium dioxide Eusolex T-2000 |  |  | 7.5 |  |  |
| Titanium dioxide T805 | 2.0 |  |  | 8.0 |  |
| Titanium dioxide Eusolex T-Aqua |  |  | 0.5 |  | 10.0 |
| Zinc oxide HP1 | 2.0 |  |  |  |  |
| Zinc oxide NDM |  | 5.5 |  | 9.5 |  |
| Zinc oxide Neutral |  | 2.00 | 1.50 |  |  |
| Zinc oxide MZ-303S | 1.00 |  | 2.5 |  | 2.00 |
| Mineral oil |  |  | 10.0 |  | 8.00 |
| C12–15 alkyl benzoate |  |  |  | 9.00 |  |
| Dicaprylyl ether | 10.00 |  |  |  | 7.00 |
| Butylene glycol dicaprylate/dicaprate |  |  | 2.00 | 8.00 | 4.00 |
| Dicaprylyl carbonate | 5.00 |  | 6.00 |  |  |
| Dimethicone |  | 4.00 | 1.00 | 5.00 |  |
| Cyclomethicone | 2.00 | 25.00 |  |  | 2.00 |
| Shea butter |  |  | 3.00 |  |  |
| PVP hexadecene copolymer | 0.50 |  |  | 0.50 | 1.00 |
| Tricontanyl PVP |  |  | 0.50 | 1.00 | 0.50 |
| Ethylhexylglycerol |  | 0.30 | 1.00 |  | 0.50 |
| Glycerol | 3.00 | 7.50 |  | 7.50 | 2.50 |
| Glycine soya |  |  | 1.00 | 1.50 |  |
| MgSO$_4$ | 1.00 | 0.50 |  | 0.50 |  |
| MgCl$_2$ |  |  | 1.00 |  | 0.70 |
| Vitamin E acetate | 0.50 |  | 0.25 |  | 1.00 |
| Styrene/acrylate copolymer | 0.50 |  |  | 2.50 |  |
| Polyurethane |  |  | 0.50 | 1.50 |  |
| DMDM hydantoin |  | 0.60 | 0.40 | 0.20 |  |
| Methylparaben | 0.50 |  | 0.25 | 0.15 |  |
| Phenoxyethanol | 0.50 | 0.40 |  | 1.00 | 0.60 |

-continued

|  | 1 | 2 | 3 | 4 | 5 |
|---|---|---|---|---|---|
| Ethanol |  |  | 3.00 |  | 1.50 |
| Perfume | 0.20 | 0.20 | 0.20 | 0.20 | 0.20 |
| Water | ad 100 | ad 100 | ad 100 | ad 100 | ad 100 |

4. Solid-Stabilized Emulsions

|  | 1 | 2 | 3 | 4 | 5 |
|---|---|---|---|---|---|
| Mineral oil |  |  |  | 16.0 | 16.0 |
| Octyldodecanol | 9.0 | 9.0 | 5.0 |  |  |
| Caprylic/capric triglyceride | 9.0 | 9.0 | 6.0 |  |  |
| C12–15 alkyl benzoate |  |  |  | 5.0 | 8.0 |
| Butylene glycol dicaprylate/dicaprate |  |  |  |  | 8.0 |
| Dicaprylyl ether | 9.0 |  |  | 4.0 |  |
| Dicaprylyl carbonate |  | 9.0 |  |  |  |
| Hydroxyoctacosanyl hydroxystearate | 2.0 | 2.0 | 2.0 | 2.0 | 1.5 |
| Disteardimonium hectorite | 1.0 | 0.75 | 0.5 | 0.5 | 0.25 |
| Microcrystalline wax + liquid paraffin |  |  |  |  | 5.0 |
| Hydroxypropyl methylcellulose |  |  |  |  | 0.05 |
| Dimethicone |  |  |  |  | 3.0 |
| Butyl methoxydibenzoylmethane | 2.00 | 0.50 | 3.50 | 1.50 | 0.50 |
| Ethylhexyl methoxycinnamate |  |  |  |  | 3.0 |
| 4-methylbenzylidene camphor |  |  |  |  | 4.0 |
| Diethylhexyl butamido triazone |  |  |  |  | 4.0 |
| Methylene bis-benzotriazolyl tetramethylbutylphenol | 0.50 |  |  | 2.0 |  |
| Drometrizole trisiloxane |  | 0.50 |  | 1.00 |  |
| Terephthalidene dicamphor sulfonic acid |  | 1.00 | 0.50 |  | 1.50 |
| Disodium phenyl dibenzimidazole tetrasulfonate | 2.50 | 2.00 | 3.10 | 1.50 | 0.50 |
| Titanium dioxide + alumina + simethicone + water |  | 2.0 | 4.0 | 2.0 | 4.0 |
| Titanium dioxide + trimethoxy-caprylylsilane |  |  |  |  | 3.0 |
| Zinc oxide HP1 |  |  |  | 6.0 |  |
| Zinc oxide MZ-303S | 2.0 |  | 3.5 |  |  |
| Silica dimethyl silylate |  |  | 1.0 |  |  |
| Boron nitride | 2.0 |  |  |  |  |
| Starch/sodium metaphosphate polymer |  | 0.5 |  |  |  |
| Diethylhexyl 2,6-naphthalate | 5.00 | 7.00 | 8.50 | 3.00 | 4.50 |
| Tapioca starch |  |  |  |  | 1.0 |
| Polyurethane | 0.20 |  | 1.50 | 0.50 |  |
| Styrene/acrylate copolymer |  | 2.00 |  |  | 3.00 |
| Sodium chloride | 1.0 | 1.0 | 1.0 | 1.0 | 1.0 |
| Glycerol | 5.0 | 10.0 | 3.0 | 6.0 | 10.0 |
| Trisodium EDTA |  | 1.0 |  | 1.0 |  |
| Methylparaben | 0.21 |  |  |  | 0.2 |
| Propylparaben | 0.07 |  |  |  |  |
| Phenoxyethanol | 0.5 |  | 0.4 | 0.4 | 0.5 |
| Hexamidine diisethionate |  |  |  |  | 0.08 |
| Diazolidinyl urea |  |  | 0.28 | 0.28 |  |
| Alcohol |  |  |  | 2.5 |  |
| Perfume | q.s. | q.s. | q.s. | q.s. | q.s. |
| Water | ad 100 | ad 100 | ad 100 | ad 100 | ad 100 |

|  | 6 | 7 | 8 | 9 | 10 |
|---|---|---|---|---|---|
| Mineral oil |  |  |  |  | 16.0 |
| Octyldodecanol | 6.0 |  | 7.5 | 7.5 | 5.0 |
| Caprylic/capric triglyceride |  |  |  |  | 6.0 |
| C12–15 alkyl benzoate | 7.0 | 8.0 | 7.5 | 7.5 |  |
| Butylene glycol dicaprylate/dicaprate | 4.0 | 8.0 |  |  |  |
| Dicaprylyl ether |  |  | 8.0 | 7.5 | 7.5 |
| Dicaprylyl carbonate | 4.0 |  |  |  |  |
| Hydroxyoctacosanyl hydroxystearate | 2.0 | 2.0 | 2.0 | 2.0 | 1.5 |
| PVP/hexadecene copolymer |  |  |  | 1.0 | 0.7 |
| Disteardimonium hectorite | 1.0 | 1.0 | 1.0 | 0.5 | 1.0 |
| Dimethicone |  | 2.0 |  |  |  |
| Cyclomethicone |  |  |  | 2.0 |  |
| Ethylhexyl methoxycinnamate | 5.0 |  | 5.0 |  |  |
| Butyl methoxydibenzoylmethane | 3.00 | 2.0 | 0.50 | 1.80 | 1.0 |
| 4-Methylbenzylidene camphor |  | 4.0 |  |  | 2.0 |
| Ethylhexyltriazone | 2.0 | 2.0 |  |  | 1.0 |
| Methylene bis-benzotriazolyl tetramethylbutylphenol |  | 3.00 |  | 2.50 |  |
| Bis-Ethylhexyloxyphenol methoxyphenyl triazine | 2.5 |  | 2.5 |  |  |
| Titanium dioxide + alumina + simethicone + water | 1.5 | 2.0 | 4.0 | 0.5 | 1.5 |
| Titanium dioxide + trimethoxy-caprylylsilane |  |  | 2.0 |  |  |
| Zinc oxide HP1 | 3.5 |  | 2.0 |  | 2.5 |
| Zinc oxide NDM |  | 2.5 |  | 4.5 |  |
| Phenylbenzimidazole sulfonic acid | 2.0 |  |  |  |  |
| Disodium phenyl dibenzimidazole tetrasulfonate | 2.50 | 1.00 | 0.60 | 1.50 | 3.00 |
| Boron nitride |  |  |  |  | 0.5 |
| Starch/sodium metaphosphate polymer | 0.5 |  | 1.5 |  |  |
| Corn starch modified |  | 1.0 |  |  |  |
| Acrylate copolymer |  |  |  | 0.25 |  |
| Talc |  |  |  | 2.0 |  |
| Sodium chloride | 1.0 | 1.0 | 1.0 |  |  |
| Diethylhexyl 2,6-naphthalate | 4.00 | 6.50 | 7.50 | 9.50 | 5.00 |
| Polyurethane |  | 0.50 | 1.50 |  | 0.40 |
| Styrene/acrylate copolymer | 1.50 |  |  |  | 3.00 |
| Magnesium sulfate |  |  |  |  | 0.70 |
| 45% sodium hydroxide solution | 0.5 | 0.5 |  |  |  |
| Glycerol | 5.0 | 7.5 | 5.0 | 10.0 | 3.0 |
| Trisodium EDTA |  | 1.0 | 1.0 |  | 1.0 |
| Propylene carbonate | 0.33 | 0.33 | 0.33 |  | 0.33 |
| Methylparaben | 0.21 | 0.21 | 0.2 | 0.2 | 0.21 |
| Propylparaben | 0.07 | 0.07 |  |  | 0.07 |
| Phenoxyethanol | 0.5 | 0.5 | 0.5 | 0.5 | 0.5 |
| Hexamidine diisethionate |  |  |  | 0.08 | 0.08 |
| Alcohol |  | 5.0 |  |  |  |
| Perfume | q.s. | q.s. | q.s. | q.s. | q.s. |
| Water | ad 100 | ad 100 | ad 100 | ad 100 | ad 100 |

The which is claimed:

1. A cosmetic or dermatological formulation comprising:
    (a) at least one particulate UV filter substance, the at least one particulate UV filter substance is a micronized inorganic pigment, and
    (b) at least one dialkyl naphthalate having the structural formula

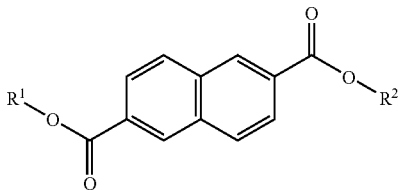

wherein $R^1$ and $R^2$ are selected independently of one another from the group consisting of branched and unbranched alkyl groups having 6 to 24 carbon atoms.

2. The formulation as claimed in claim 1, wherein at least one of $R^1$ and $R^2$ is a branched alkyl group having 6 to 10 carbon atoms.

3. The formulation as claimed in claim 1, wherein $R^1$ and $R^2$ are branched alkyl groups having 6 to 10 carbon atoms.

4. The formulation as claimed in claim 1, wherein the at least one dialkyl naphthalate comprises diethylhexyl naphthalate.

5. The formulation as claimed in claim 1, wherein the at least one dialkyl naphthalate is present in amount of 0.001 to 20 weight % based on the total weight of the formulation.

6. The formulation as claimed in claim 5, wherein the at least one dialkyl naphthalate is present in an amount of 0.01 to 15 weight % based on the total weight of the formulation.

7. The formulation as claimed in claim 5, wherein the at least one dialkyl naphthalate is present in an amount of 3 to 10 weight % based on the total weight of the formulation.

8. The formulation as claimed in claim 1, wherein the micronized inorganic pigment is a micronized metal oxide.

9. The formulation as claimed in claim 8, wherein the micronized metal oxide is an oxide of a metal selected from the group consisting of titanium, zinc, iron, zirconium, silicon, manganese, aluminum, cerium, and mixtures thereof.

10. The formulation as claimed in claim 8, wherein the micronized metal oxide further comprises barium sulfate.

11. The formulation as claimed in claim 8, wherein the micronized metal oxide has a primary particle size of less than 300 nm.

12. The formulation as claimed in claim 11, wherein the micronized metal oxide has a primary particle size of 10 to 150 nm.

13. The formulation as claimed in claim 8, wherein the micronized metal oxide is a surface treated metal oxide.

14. The formulation as claimed in claim 1, wherein the at least one UV filter substance is present in an amount of 0.01 to 20 weight % based on the total weight of the formulation.

15. The formulation as claimed in claim 14, wherein the at least one UV filter substance is present in an amount of 0.1 to 8 weight % based on the total weight of the formulation.

16. The formulation as claimed in claim 1, further comprising at least one additional UV filter substance selected from the group consisting of triazines, benzotriazoles, organic, inorganic pigments, and mixtures thereof.

17. The formulation as claimed in claim 1, further comprising at least one UV-A filter substance or broad-band filter substance.

18. The formulation as claimed in claim 17, wherein said at least one UV-A filter substance or broad-band filter substance includes at least one dibenzoylmethane derivative.

19. The formulation as claimed in claim 18, wherein the dibenzoylmethane derivative is selected from the group consisting of 4-(tert-butyl)-4'-methoxydibenzoylmethane, 2,4-bis{[4-(2-ethylhexyloxy)-2--hydroxy]phenyl}-6-(4-methoxyphenyl)-1,3,5-triazine, and mixtures thereof.

20. The formulation as claimed in claim 1, wherein the formulation is an oil-in-water emulsion.

21. The formulation as claimed in claim 1, wherein the formulation is a water-in-oil emulsion.

22. The formulation as claimed in claim 1, wherein the formulation is a hydrodispersion.

23. The formulation as claimed in claim 1, wherein the formulation is a solid stabilized emulsion.

24. A method for moisturizing skin comprising applying to the skin a cosmetic or dermatological formulation comprising:
(a) at least one particulate UV filter substance, the at least one particulate UV filter substance is a micronized inorganic pigment, and
(b) at least one dialkyl naphthalate having the structural formula

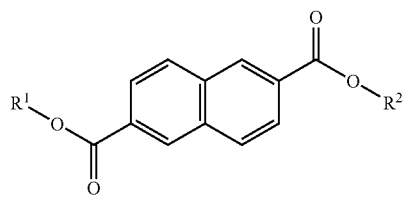

wherein $R^1$ and $R^2$ are selected independently of one another from the group consisting of branched and unbranched alkyl groups having 6 to 24 carbon atoms.

25. A method for protecting skin from light-induced skin aging comprising applying to the skin a cosmetic or dermatological formulation comprising:
(a) at least one particulate UV filter substance, the at least one particulate UV filter substance is a micronized inorganic pigment, and
(b) at least one dialkyl naphthalate having the structural formula

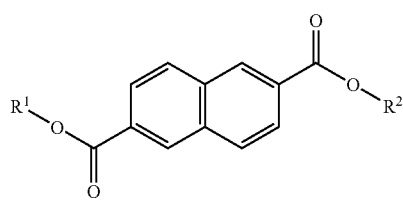

wherein $R^1$ and $R^2$ are selected independently of one another from the group consisting of branched and unbranched alkyl groups having 6 to 24 carbon atoms.

26. A method for increasing the UV protection of a cosmetic or dermatological formulation comprising at least one particulate UV filter substance, said method comprising adding to the cosmetic or dermatological formulation at least one dialkyl naphthalate having the structural formula

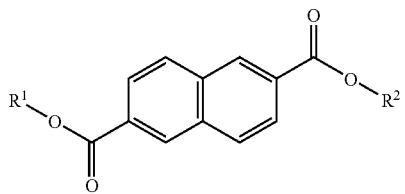
wherein $R^1$ and $R^2$ are selected independently of one another from the group consisting of branched and unbranched alkyl groups having 6 to 24 carbon atoms and the at least one particulate UV filter substance is a micronized inorganic pigment.
* * * * *